United States Patent

Greindl et al.

[11] Patent Number: 5,907,055
[45] Date of Patent: May 25, 1999

[54] USE OF TRIACIDS BASED ON ALKOXYLATED TERTIARY AMINES AS COMPLEXING AGENTS

[75] Inventors: Thomas Greindl, Neuburg; Birgit Potthoff-Karl, Ludwigshafen; Alfred Oftring, Bad Dürkheim; Thomas Fetzer, Speyer; Richard Baur, Mutterstadt; Wolfgang Trieselt, Karlsruhe, all of Germany

[73] Assignee: BASF Aktiengesellschaft, Ludwigshafen, Germany

[21] Appl. No.: 08/875,347

[22] PCT Filed: Jan. 17, 1996

[86] PCT No.: PCT/EP96/00169

§ 371 Date: Jul. 28, 1997

§ 102(e) Date: Jul. 28, 1997

[87] PCT Pub. No.: WO96/22964

PCT Pub. Date: Aug. 1, 1996

[30] Foreign Application Priority Data

Jan. 26, 1995 [DE] Germany .......................... 195 02 294

[51] Int. Cl.⁶ .................................................. C07C 51/16
[52] U.S. Cl. ............................................. 562/526; 562/568
[58] Field of Search ...................... 562/526, 568

[56] References Cited

U.S. PATENT DOCUMENTS

| | | |
|---|---|---|
| 2,316,636 | 4/1943 | Teeters . |
| 5,292,936 | 3/1994 | Franczyk .................................. 562/526 |
| 5,367,112 | 11/1994 | Franczyk .................................. 562/526 |

OTHER PUBLICATIONS

CA:120:288467 by Rissanen in Supramol Chem 2 (2–3) pp. 247–250, 1993.

Beilstein reg no 1748627, prep of in Bull Soc Chim Fr 287, 1953.

*Primary Examiner*—Gary Geist
*Assistant Examiner*—Jean F. Vollano
*Attorney, Agent, or Firm*—Oblon, Spivak, McClelland, Maier & Neustadt, P.C.

[57] ABSTRACT

The use of triacids of the formula I

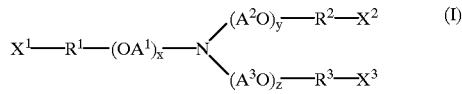

where
- $X^1$ to $X^3$ are, independently of one another, carboxylic acid groups of the formula COOM, sulfonic acid groups of the formula $SO_3M$ or phosphonic acid groups of the formula $PO_3M_2$, where
- M is hydrogen, alkali metal, ammonium or substituted ammonium,
- $A^1$ to $A^3$ are, independently of one another, 1,2-alkylene with 2 to 18 carbon atoms,
- $R^1$ to $R^3$ are, independently of one another, $C_1$–$C_8$-alkylene, and
- x, y and z are, independently of one another, a number from 0 to 10, where the total of x+y+z must be greater than or equal to 1, as complexing agents for complexing heavy metals or for preparing heavy metal complexes for changing the redox potential, and as builders in detergents and cleaners.

2 Claims, No Drawings

/ 1

USE OF TRIACIDS BASED ON ALKOXYLATED TERTIARY AMINES AS COMPLEXING AGENTS

This application is the national phase of PCT/EP96/00169 filed Jan. 17, 1996.

BACKGROUND OF THE INVENTION

1. Field of the Invention

The present invention relates to the use of triacids of the formula I $$X^1-R^1-(OA^1)_x-N\begin{matrix}(A^2O)_y-R^2-X^2\\(A^3O)_z-R^3-X^3\end{matrix} \quad (I)$$

where $X^1$ to $X^3$ are, independently of one another, carboxylic acid groups of the formula COOM, sulfonic acid groups of the formula $SO_3M$ or phosphonic acid groups of the formula $PO_3M_2$, where M is hydrogen, alkali metal, ammonium or substituted ammonium, $A^1$ to $A^3$ are, independently of one another, 1,2-alkylene with 2 to 18 carbon atoms, $R^1$ to $R^3$ are, independently of one another, $C_1$–$C_8$-alkylene, and x, y and z are, independently of one another, a number from 0 to 10, where the total of $x+y+z$ must be greater than or equal to 1, as complexing agents for complexing heavy metals or for preparing heavy metal complexes for changing the redox potential, and as builders in detergents and cleaners.

Since some of the compounds I are novel substances, the invention furthermore relates to these novel substances. The invention additionally relates to processes for preparing the triacids I and to the use of intermediates arising therein and the preparation thereof.

2. Description of the Background

The complexing agents employed for heavy metal ions in a wide variety of industrial sectors, in which the ranges of requirements and problems in some cases differ greatly from one another, are still usually the long-known and proven systems such as polyphosphates, nitrilotriacetic acid or ethylenediaminetetraacetic acid. However, these agents have certain disadvantages, the principal weaknesses being in particular that their heavy metal binding capacity is still in need of improvement, their stabilizing effect in bleaching baths and bleaching systems is not yet optimal, and their biodegradability and elimination capacity are usually inadequate.

U.S. Pat. No. 2,316,636 describes a process for preparing aminopolycarboxylic acids and their salts from the underlying amino alcohols. Specific aminopolycarboxylic acids mentioned are, inter alia, the compounds $$MOOC-CH_2-O-CH_2CH_2-N\begin{matrix}CH_2-COOM\\CH_2-COOM\end{matrix},$$

-continued $$MOOC-CH_2-O-CH_2CH_2-N\begin{matrix}CH_2CH_2-O-CH_2-COOM\\CH_2-COOM\end{matrix} \text{ and}$$

$$MOOC-CH_2-O-CH_2CH_2CH_2-N\begin{matrix}CH_2CH_2CH_2-O-CH_2-COOM\\CH_2-COOM\end{matrix}.$$

Aminopolycarboxylic acids of these types are recommended for the industrial sectors of detergents and laundry aids, of water softening, of water treatment and of textile bleaching.

SUMMARY OF THE INVENTION

It is an object of the present invention to provide complexing agents which no longer have the disadvantages of the prior art.

We have found that this object is achieved by the above-defined use of the triacids I.

DETAILED DESCRIPTION OF THE INVENTION

The described triacids I based on alkoxylated tertiary amines can be employed both in the form of the free acids (M=hydrogen) and in the form of their mono-, di- or trisalts (in the case of carboxylic or sulfonic acids) or mono- to hexasalts (in the case of phosphonic acids).

Particularly suitable salts of these types are the sodium, potassium and ammonium salts, especially (in the case of carboxylic or sulfonic acids) the trisodium, tripotassium and triammonium salt, and organic triamine salts with a tertiary nitrogen atom.

Suitable bases underlying the organic amine salts are, in particular, tertiary amines such as trialkylamines with 1 to 4 carbon atoms in the alkyl, such as trimethyl- and triethylamine, and trialkanolamines with 2 or 3 carbon atoms in the alkanol residue, preferably triethanolamine, tri-n-propanolamine or triisopropanolamine.

Preferred triacids I are those where $X^1$ to $X^3$ are carboxylic acid groups of the formula COOM.

Suitable and preferred 1,2-alkylene groups $A^1$ to $A^3$ are those with 2 to 4 carbon atoms, in particular groups derived from ethylene oxide, propylene oxide or butylene oxide. $A^1$ to $A^3$ are preferably 1,2-ethylene or 1,2-propylene. However, $A^1$ to $A^3$ can also be larger groups, for example those derived from styrene oxide or longchain epoxides such as decene oxide or dodecene oxide.

Particularly suitable $C_1$–$C_8$-alkylene groups $R^1$ to $R^3$ are linear or branched $C_1$–$C_4$-alkylene groups, but especially methylene, 1,1-ethylene, 1,1-propylene and 1,2-ethylene.

The variables x, y and z are preferably independently of one another a number from 0 to 5, in particular 0 to 3. Particularly preferred triacids I are those in which these variables have the following meanings:

x=1, y=0, z=0 or
x=1, y=1, z=0 or
x=1, y=1, z=1 or
x=2, y=0, z=0 or
x=2, y=2, z=0 or
x=2, y=2, z=2.

Further preferred triacids I are those in which the variables $X^1$ to $X^3$ and/or $A^1$ to $A^3$ and/or $R^1$ to $R^3$ are in each case identical.

Of particular interest for the use according to the invention of the described triacids I are the complexing and the heavy metal complexes of iron, copper, zinc and manganese, but also of chromium, cadmium, nickel, silver, gold and mercury. The triacids I are also suitable as builders in conventional detergents and cleaners, especially in textile detergent formulations.

The described triacids I are preferably employed as heavy metal complexing agents in bleaching baths in the paper industry, in detergents and cleaners, in cosmetic or pharmaceutical formulations, in soap manufacture, in crop nutrition and for preparing metal complexes for use in electroplating baths or in the desulfurization of flue gases. In electroplating baths and in the desulfurization of flue gases, the metal complexes based on the triacids I are used to change the redox potential of the particular metals.

Another preferred use of the triacids I is that in the form of the manganese complexes as bleach activators in detergents and cleaners, especially in textile detergent formulations.

A preferred use of the triacids I and their salts is in bleaching baths in the paper industry. In this case, complexing agents are required in reductive bleaching, eg. with sodium dithionite, or in oxidative bleaching, eg. with hydrogen peroxide, in order to increase the efficiency of the bleaching process, ie. the whiteness of the groundwood pulp. The complexing agents are thus used to eliminate heavy metal cations, mainly of iron, copper and, in particular, manganese, which also interfere with resin sizing using alum and sodium resinate owing to information of insoluble salts. Deposition of iron on paper leads to hot spots where oxidative catalytic decomposition of cellulose starts.

A typical formulation of such an aqueous reductive bleaching bath in the paper industry for groundwood pulp (4% consistency, for example) contains 0.05 to 0.1% by weight of complexing agent I and about 1% by weight of sodium dithionite, in each case based on the groundwood pulp. The bath temperature is about 60° C., the bleaching time is normally 1 hour and the pH is about 5.8.

A typical formulation of such an aqueous oxidative bleaching bath in the paper industry for groundwood pulp (20% consistency, for example) contains 0.05 to 0.15% by weight of complexing agent I, about 2% by weight of water glass, about 0.75% by weight of NaOH and about 1% by weight of $H_2O_2$, in each case based on the groundwood pulp. The bath temperature is about 50° C. and the bleaching time is normally 2 hours.

The triacids I and their salts are mainly employed in pharmaceuticals and cosmetics in order to prevent olefinic double bonds being oxidised, with catalysis by heavy metals, and thus the products becoming rancid.

In soaps, they prevent oxidative decomposition catalyzed by heavy metals.

In crop nutrition, the preferred use is of copper, iron, manganese and zinc complexes of the triacids I to eliminate heavy metal deficiencies. The heavy metals are thus added as chelates in order to avoid precipitation as biologically inactive, insoluble salts.

A preferred use of the triacids I and their salts in electroplating baths is mainly to sequester contaminating heavy metal cations. In this case, they replace the highly toxic cyanides.

A typical composition which may be mentioned for such an aqueous electroplating bath for depositing, for example, copper, nickel, zinc or gold is the following copper bath:

about 10 g/l copper(II) sulfate pentahydrate

10–12 g/l formaldehyde

12–15 g/l complexing agent I

1–2 g/l of $C_{13}/C_{15}$ oxo alcohol which has been reacted with 12 mol of ethylene oxide and 6 mol of propylene oxide, as wetting agent.

This bath is normally adjusted to pH 13 with sodium hydroxide solution; it may also contain conventional stabilizers such as amines or sodium cyanide.

An advantageous effect of the triacids I and their salts is in the stabilization of bleaches, for example in the bleaching of textiles, pulp or stock. Traces of heavy metals such as iron, copper and manganese occur in the components of the bleaching bath itself, in the water and in the material to be bleached, and catalyze the decomposition of the bleach. The complexing agents I bind these metal ions and prevent unwanted decomposition of the bleaching system during storage and use. This increases the efficiency of the bleaching system and damage to the material to be bleached is diminished.

The triacids I and their salts are particularly suitable for the described purposes of use because they are extremely efficient complexing agents for heavy metal ions, especially for iron, copper, zinc and manganese. Their binding capacities for iron, copper, zinc and manganese are exceptionally high. It is possible in particular, by varying the adjustment of the degrees of alkoxylation x, y and z, to control the selectivity for individual heavy metal ions in a specific manner.

Further advantages are their very low toxicity potential and their good biodegradability. Thus, in the Zahn-Wellens test under standard conditions, the biodegradability of most of the triacids I, eg. those with x=1 or 2 and y=z=0, is >90% (after 28 days), whereas that for ethylenediaminetetraacetic acid, for example, under the same conditions is <10%.

Some of the compounds I are novel substances. The present invention therefore also relates to triacids of the formula I with the exception of the compounds

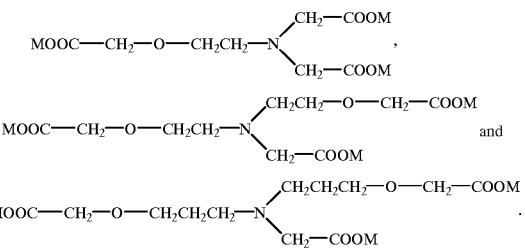

Triacids I where $X^1$ is a carboxylic acid group of the formula COOM and $x \geq 1$, y=0 and z=0, or where $X^1$ and $X^2$ are carboxylic acid groups of the formula COOM and $x \geq 1$, $y \geq 1$ and z=0, are advantageously prepared by catalytic oxidation of amino alcohols of the formula IIa or IIb

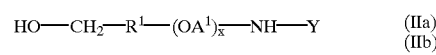

(IIa)
(IIb)

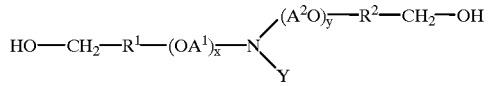

where Y is a protective group, to the corresponding amino carboxylic acids of the formula IIIa or IIIb

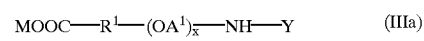

(IIIa)

-continued

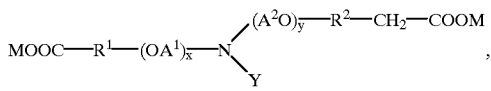
(IIIb)

elimination of the protective groups Y, and conversion of the free amino group by conventional methods into the corresponding N-alkylenecarboxylic, -sulfonic or -phosphonic acid group.

Oxidation of structures IIa and IIb to IIIa and IIIb, respectively, is usually carried out in liquid phase with air or oxygen on a platinum metal catalyst, preferably on a platinum or palladium catalyst, with the noble metal preferably being present on active carbon as carrier material. Other platinum metals which can be used are ruthenium, rhodium, osmium or iridium. It is also possible to employ mixtures of different platinum metals. This is normally carried out at from 20° C. to 100° C., under from 0.1 to 10 bar and at pH 5–12; preferably 40–80° C., 0.2–1.0 bar and pH 8–11.

The acetyl group is preferably used as protective group Y. This can be introduced, for example, by reaction with acetic anhydride, and can be eliminated again with alkali. However, it is also possible to employ amide-, imide- or urethane-protected starting compounds in a conventional way.

Particularly suitable for converting the free amino groups into N-alkylenecarboxylic acid groups are reaction with halo carboxylic acids such as chloroacetic acid, bromoacetic acid, chloropropionic acid or bromopropionic acid or the Strecker reaction using hydrogen cyanide and the appropriate aldehyde such as formaldehyde or acetaldehyde.

Triacids I where $X^1$ to $X^3$ are carboxylic acid groups of the formula COOM, the variables $R^1$ to $R^3$ are methylene, 1,1-ethylene or 1,1-propylene, and $x \geq 1$, $y \geq 1$ and $z \geq 1$, are advantageously prepared by reacting amino triols of the formula IV

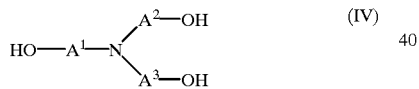
(IV)

with alkylene oxide until the degree of alkoxylation x or y or z is as required, and catalytically oxidizing the terminal hydroxyl groups to the corresponding carboxylic acids. This process is particularly favorable because it permits a large number of tricarboxylic acids I to be synthesized starting from starting materials which are readily available at reasonable cost. In addition, the products are chlorine-free and the ion selectivity of the complexing agents can be controlled by the degree of alkoxylation.

The oxidation is normally carried out in liquid phase with air or oxygen or under dehydrogenating conditions with hydrogen, which may be diluted with nitrogen, on a copper catalyst or on a catalyst consisting of a mixture of copper and platinum metals, ie. ruthenium, rhodium, osmium, iridium or, in particular, platinum or palladium, with the catalyst preferably being present on zirconium dioxide as carrier material. This is normally carried out at from 100 to 230° C. under from 1 to 30 bar, preferably at 120–200° C. under 2–20 bar.

Alkoxylation of IV with butylene oxide or, preferably, ethylene oxide or propylene oxide normally affords random mixtures in which the degrees of alkoxylation, as generally in compounds I, represent a random distribution. These mixtures are normally employed just as they are obtained.

The described synthetic sequence starts from readily available and low-cost starting materials and affords the required final products in high yields, selectivity and purities. Moreover the amount of unwanted byproducts, eg. of inorganic salts, is low.

The present invention likewise relates to the amino carboxylic acids of the formula Va and Vb

 (Va)

 (Vb)

where the variables $R^1$, $R^2$, $A^1$, $A^2$, M, x and y have the abovementioned meanings, which are produced in the conversion of IIIa and IIIb, respectively, into the triacids I, as intermediates for preparing the triacids I.

The amino carboxylic acids Va and Vb can be prepared particularly advantageously by subjecting amino alcohols IIa and IIb, respectively, to a catalytic oxidation in the presence of an oxidation catalyst based on copper or a mixture of copper and platinum metals, ie. ruthenium, rhodium, osmium, iridium or, in particular, platinum or palladium. The present invention thus also relates to this process. The advantages of this process are the use of precursors available at reasonable cost, without toxicity problems and with wide variability, the avoidance of organic chlorine compounds as basis for the synthesis, and the high yields in most cases. It is thus possible to obtain such amino carboxylic acids at reasonable cost also for use in pharmaceutical agents.

SYNTHETIC EXAMPLES

Process A

Preparation of the Triacids I via Synthesis of Polyether Amino Carboxylic Acids IIIa/b Example A1

5-bis(carboxymethyl)amino-3-oxapentanoic acid

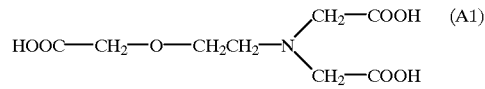 (A1)

A1.1: Sodium 5-acetylamino-3-oxapentanoate 73.5 g of 5-acetylamino-3-oxa-1-pentanol were dissolved in 425 g of water, and 2.90 g of Pd/C (10% by weight) were added. The solution was heated to 70° C. and, while stirring vigorously, about 50 ml/min $O_2$ were passed continuously through the solution under atmospheric pressure for 5 h. Throughout the reaction, the pH was kept at 10 by continuously metering in a total of 116 g of 20% by weight aqueous NaOH. The remaining solution was then extracted with ethyl acetate in a perforator for 3 days. The aqueous phase was then distilled to dryness to leave 77.8 g (corresponding to 85% of theory) of NMR-pure sodium 5-acetylamino-3-oxapentanoate.

A1.2: Sodium 5-amino-3-oxapentanoate 52 g of sodium 5-acetylamino-3-oxapentanoate were dissolved in 200 ml of water. 11.4 g of NaOH were added at 20° C., and the reaction mixture was then heated at 100° C. for 8 h until precursor was no longer detectable. Then 200 ml of EtOH were added and the pH was adjusted to about 6, resulting in pure crystals of sodium 5-amino-3-oxapentanoate. The crude product resulting after removal of the solvent by distillation as a mixture with sodium acetate weighing 63.3 g (corresponding to 100% of theory) could be employed without prior precipitation for the subsequent reaction.

A1.3: 5-Bis(carboxymethyl)amino-3-oxapentanoic acid 18.9 g of the above sodium 5-amino-3-oxapentanoate were dissolved in 100 g of water and, at 65° C., a solution of 31.2 g of sodium chloroacetate in 50 g of water was added dropwise over the course of 1 h, simultaneously keeping the pH of the solution at 8.5 by adding a total of 21.4 g of 50% by weight NaOH. After reaction for 4 h, the pH was adjusted to 2 with 23.4 g of 37% by weight aqueous hydrochloric acid, the solvent was distilled off under reduced pressure, the residue was dissolved in dimethylformamide, and precipitated and NCl was filtered off. The remaining mother liquor was slowly added dropwise to 1 l of ethanol, resulting in 21.7 g of product (corresponding to 96% of theory) as a colorless powder with an iron-binding capacity of 3.76 mmol/g.

Example A2

Trisodium 8-bis(carboxylatomethyl)amino-3,6-dioxaoctanoate (A2)

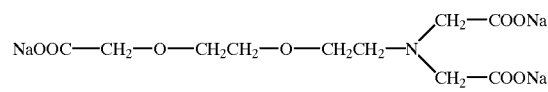

A2.1: Sodium 8-acetylamino-3,6-dioxaoctanoate 95.5 g of 8-acetylamino-3,6-dioxa-1-octanol were dissolved in 405 g of water, and 2.90 g of Pd/C (10% by weight) were added. The solution was heated to 70° C. and, while stirring vigorously, about 17 ml/min $O_2$ were passed continously through the solution under atmospheric pressure for 14 h. Throughout the reaction, the pH was kept at 10 by continuously metering in a total of 105 g of 20% by weight aqueous NaOH. The remaining solution was then extracted with ethyl acetate in a perforator for 3 days. The aqueous phase was then distilled to dryness to leave 106 g (corresponding to 94% of theory) of sodium 8-acetylamino-3,6-dioxaoctanoate as viscous oil.

A2.2: 8-Amino-3,6-dioxaoctanoic acid 63.5 g of sodium 8-acetylamino-3,6-dioxaoctanoate were dissolved in 200 ml of water. 11.2 g of NaOH were added at 20° C., and the reaction mixture was then heated at 100° C. for 8 h until precursor was no longer detectable. The pH was then adjusted to 6 with 53.7g of 37% by weight aqueous hydrochloric acid, and the solvent was distilled off under reduced pressure. The oily residue was dissolved in 200 ml of ethanol and filtered to remove undissolved sodium chloride, the mother liquor was slowly added dropwise to 1 l of ethyl acetate, and the oily phase which separated out was removed and dried under reduced pressure. This resulted in 40.6 g of 8-amino-3,6-dioxaoctanoic acid (corresponding to 89% of theory).

A2.3: Trisodium 8-bis(carboxylatomethyl)amino-3,6-dioxaoctanoate 31.7 g of the above 8-amino-3,6-dioxaoctanoic acid were dissolved in 80 g of water and, at 65° C., a solution of 39.9 g of sodium chloroacetate in 50 g of water was added dropwise over the course of 1 h, simultaneously keeping the pH of the solution at 8.5 by adding a total of 45 g of 50% by weight NaOH. After reaction for 4 h, the solvent was distilled off under reduced pressure, the residue was digested with hot ethanol, and undissolved NaCl was filtered off. After removal of the ethanol by distillation, 52.3 g of trisodium 8-bis(carboxylatomethyl)amino-3,6-dioxaoctanoate remained as colorless hygroscopic crystals with a calciumbinding capacity of 2.8 mmol/g, corresponding to a yield of 89%.

Example A3

Mixture of trisodium 8-bis(carboxylatomethyl)amino-3,6-dioxanonanoate and trisodium 8-bis(carboxylatomethyl)amino-3,6-dioxa-7-methyl-octanoate (A3)

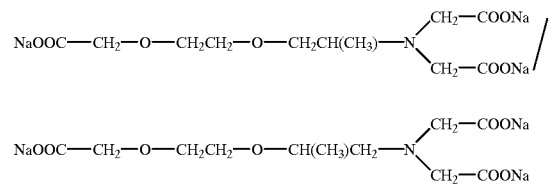

A3.1: Sodium 8-acetylamino-3,6-dioxanonanoate/sodium 8-acetylamino-3,6-dioxa-7-methyloctanoate 103 g of a mixture of 8-acetylamino-3,6-dioxa-1-nonanol and 8-acetylamino-3,6-dioxa-7-methyl-1-octanol were dissolved in 400 g of water, and 2.90 g of Pd/C (10% by weight) were added. The solution was heated to 70° C. and, while stirring vigorously, about 17 ml/min $O_2$ were passed continuously through the solution under atmospheric pressure for 15 h. Throughout the reaction, the pH was kept at 10 by continuously metering in a total of 111 g of 20% by weight aqueous NaOH. After removal of the catalyst by filtration, the solvent was distilled off to leave 129 g of sodium 8-acetylamino-3,6-dioxanonanoate/sodium 8-acetylamino-3,6-dioxa-7-methyloctanoate mixture as colorless oil with a purity of 88% (corresponding to 96% of theory).

A3.2: Sodium 8-amino-3,6-dioxanonanoate/sodium 8-amino-3,6-dioxa-7-methyloctanoate 94.3 g of sodium 8-acetylamino-3,6-dioxanonanoate/sodium 8-acetylamino-3,6-dioxa-7-methyloctanoate mixture were dissolved in 200 ml of water. 15.6 g of NaOH were added at 20° C., and the reaction mixture was then heated at 100° C. for 8 h until precursor was no longer detectable. The pH was then adjusted to 6 with 37.4 g of 37% by weight aqueous hydrochloric acid, and the solvent was distilled off under reduced pressure. The oily residue was dissolved in 200 ml of ethanol and filtered to remove undissolved sodium chloride, the mother liquor was slowly added dropwise to 1 l of ethyl acetate, and the oily phase which separated out was removed and dried under reduced pressure. This resulted in 64.9 g of sodium 8-amino-3,6-dioxanonanoate/8-amino-3,6-dioxa-7-methyl-octanoate mixture (corresponding to 93% of theory).

A3.3: Trisodium 8-bis(carboxylatomethyl)amino-3,6-dioxanonanoate/trisodium 8-bis(carboxylatomethyl)amino-3,6-dioxa-7-methyloctanoate 48.0 g of the above sodium 8-amino-3,6-dioxanonanoate/sodium 8-amino-3,6-dioxa-7-methyloctanoate were dissolved in 100 g of water and, at 65° C., a solution of 63.2 g of sodium chloroacetate in 50 g of water was added dropwise over the course of 1 h, simultaneously keeping the pH of the solution at 8.5 by adding a total of 61.2 g of 50% by weight NaOH. After reaction for 4 h, the solvent was distilled off under reduced pressure, the residue was digested with hot ethanol, and undissolved NaCl was filtered off. After removal of the ethanol by distillation, 88.5 g of trisodium 8-bis(carboxylatomethyl)amino-3,6- dioxanonanoate/trisodium 8-bis(carboxylatomethyl)amino-3,6-dioxa-7-methyloctanoate mixture with a calcium-binding capacity of 2.7 mmol/g (corresponding to 91% of theory) remained.

Process B

Preparation of the Triacids I by Synthesis from the Amino Triols IV

The required oxidation catalysts were prepared by known methods by coprecipitation of soluble copper compounds such as copper nitrate together with zirconyl chloride in alkaline medium, calcination and subsequent reduction of the oxide in a stream of hydrogen.

Example B1

Trisodium Salt of the Triacid Based on Triethanolamine with 4 mol of Ethylene Oxide (B1)

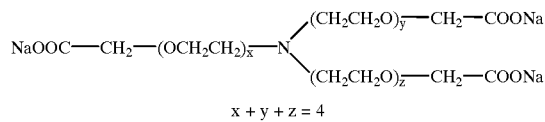

x + y + z = 4

209 g of triethanolamine and 0.4 g of potassium tert-butoxide were heated at 80° C. for 30 min under 2 mbar. Then 246 g of ethyl-ene oxide were metered over the course of 2 h into the mixture at 120° C. under pressure. Reaction for 10 h resulted in 456 g of an oil with an OH number of 531 (corresponding to 103% of theory).

32.5 g of this oil were introduced together with 50 g of water, 24.8 g of 50% by weight NaOH and 21.5 g of Cu/ZrO$_2$ catalyst (prepared by the above process by reduction of 12% by weight CuO/88% by weight ZrO$_2$ in a stream of H$_2$ at 160° C.) into a steel autoclave. The reactor was flushed twice with nitrogen and once with hydrogen and then heated at 190° C. for 10 h, discharging the hydrogen produced during the reaction. After cooling, the product solution was filtered to remove catalyst, and the mother liquor was evaporated to dryness. 42.2 g of a colorless waxy product (corresponding to 97% of theory) with a calcium-binding capacity of 2.17 mmol/g, corresponding to 94% of active substance, remained.

Example B2

Trisodium Salt of the Triacid Based on Triethanolamine with 8 mol of Ethylene Oxide (B2)

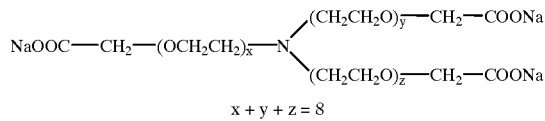

x + y + z = 8

149 g of triethanolamine and 0.3 g of potassium tert-butoxide were heated at 80° C. for 30 min under 2 mbar. Then 352 g of ethyl-ene oxide were metered over the course of 2 h into the mixture at 120° C. under pressure. Reaction for 10 h resulted in 502 g of an oil with an OH number of 364 (corresponding to 108% of theory).

25.1 g of this oil were introduced together with 50 g of water, 12.8 g of 50% by weight NaOH and 5.0 g of Cu/ZrO$_2$ catalyst (prepared by the above process by reduction of 12% by weight CuO/88% by weight ZrO$_2$ in a stream of H$_2$ at 160° C.) into a steel autoclave.

The reactor was flushed twice with nitrogen and once with hydrogen and then heated at 210° C. for 10 h, discharging the hydrogen produced during the reaction. After cooling, the product solution was filtered to remove catalyst, and the mother liquor was evaporated to dryness. 33.0 g of a colorless waxy product (corresponding to 108% of theory) with an iron-binding capacity of 1.36 mmol/g, corresponding to 83% of active substance, remained.

Processes B1 and B2 afforded identical results when ammonia, in place of triethanolamine, was reacted with 7 and 11 mol, respectively, of ethylene oxide and subsequently oxidized.

Degradation Tests

5-Bis(carboxymethyl)amino-3-oxapentanoic acid (Example A1):

Zahn-Wellens stationary test (as specified in EC Directive 88/302/EEC, OECD 302B, ISO 9888): 98% DOC elimination after 4 days (ethylene glycol control substance: DOC 98%)

Trisodium 8-bis(carboxylatomethyl)amino-3,6-dioxaoctanoate (Example A2):

Zahn-Wellens stationary test (as specified in EC Directive 88/302/EEC, OECD 302B, ISO 9888): 93% DOC elimination after 21 days (ethylene glycol control substance: DOC 98%)

Trisodium 8-bis(carboxylatomethyl)amino-3,6-dioxanonanoate/trisodium 8-bis(carboxylatomethyl)amino-3,6-dioxa-7-methyloctanoate mixture (Example A3):

Zahn-Wellens stationary test (as specified in EC Directive 88/302/EEC, OECD 302B, ISO 9888): 60% DOC elimination after 31 days (ethylene glycol control substance: DOC 98%)

Data on Use

Structure A1 has a calcium-binding capacity (Ca-BC) of 425 mg CaCO$_3$/g, a calcium carbonate dispersing capacity (CCDC) of 575 mg (20° C.) and 410 mg (80° C.); Structure A1 binds 212 mg manganese/g (cf. EDTA: 192 mg/g); Structure A1 binds 298 mg copper/g (cf. EDTA: 217 mg/g); Structure A1 binds 220 mg iron/g (cf. EDTA: 192 mg/g). (EDTA=tetrasodium ethylenediaminetetraacetate).

Structure A2 has a Ca-BC of 280 mg CaCO$_3$/g, a CCDC of 275 mg (20° C.) and 265 mg (80° C.) and binds 132 mg Mn/g, 204 mg Cu/g and 119 mg Fe/g.

Structure A3 has a Ca-BC of 290 mg CaCO$_3$/g, a CCDC of 270 mg (20° C.) and 180 mg (80° C.) and binds 105 mg Mn/g, 193 mg Cu/g and 93 mg Fe/g.

We claim:

1. A process for preparing a triacid of formula I

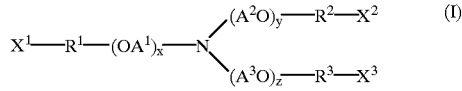

(I)

where

X$^1$, X$^2$ and X$^3$ are each a carboxylic acid group of the formula COOM;

M is hydrogen, alkali metal, ammonium or substituted ammonium;

$A^1$, $A^2$ and $A^3$ are, independently of one another, 1,2-alkylene with 2 to 18 carbon atoms;

$R^1$, $R^2$ and $R^3$ are, independently of one another, $R^1$, $R^2$ and $R^3$ are methylene, 1,1-ethylene or 1,1-propylene; and x, y and z are, independently of one another, a number from 1 to 10, which comprises reacting an amino triol of the formula IV

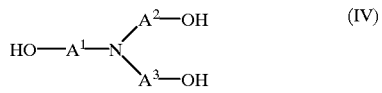 (IV)

with an alkylene oxide until the degree of alkoxylation x or y or z is as required, followed by catalytically oxidizing the terminal hydroxyl groups to the corresponding carboxylic acids.

2. A process for preparing the triacid of formula I as claimed in claim 1, wherein the oxidation catalyst is copper on zirconium dioxide or a mixture of copper and platinum metals on zirconium dioxide.

* * * * *